US00PP13383P3

(12) United States Plant Patent
Danziger

(10) Patent No.: US PP13,383 P3
(45) Date of Patent: Dec. 17, 2002

(54) PETUNIA PLANT NAMED 'DANCASOFT'

(75) Inventor: Gabriel Danziger, Nir-Zvi (IL)

(73) Assignee: Danziger "DAN" Flower Farm, Post Beit Dagan (IL)

( * ) Notice: Subject to any disclaimer, the term of this patent is extended or adjusted under 35 U.S.C. 154(b) by 0 days.

(21) Appl. No.: 09/838,231

(22) Filed: Apr. 20, 2001

(65) Prior Publication Data

US 2002/0157161 P1 Oct. 24, 2002

(51) Int. Cl.[7] ..... A01H 5/00

(52) U.S. Cl. ..... Plt./356

(58) Field of Search ..... Plt./356

*Primary Examiner*—Bruce R. Campell
*Assistant Examiner*—Annette Para
(74) *Attorney, Agent, or Firm*—Foley & Lardner

(57) ABSTRACT

A new and distinct cultivar of Petunia plant named 'Dancasoft', as described and illustrated, and particularly characterized by the combined features of pastel pink flower color, single flower type, medium flower size, early year round flowering time, spreading, well-branched vigorous growth habit, good weather tolerance, suitable for hanging baskets and bedding.

1 Drawing Sheet

LATIN NAME OF THE GENUS AND SPECIES OF THE CLAIMED PLANT

*Petunia hybrida.*

VARIETY DENOMINATION

Dancasoft.

BACKGROUND OF THE INVENTION

The present invention comprises a new and distinct cultivar of petunia, known by the cultivar name 'Dancasoft'.

'Dancasoft' originated from a hybridization made by the inventor in a controlled breeding program in Mishmar Hashiva Israel in 1998. The female was Chipper® by Danziger (unpatented). The male parent of 'Dancasoft' was 'CV. 322' (unpatented).

'Dancasoft' was discovered and selected as one flowering plant within the progeny of the stated cross by or under the supervision of the inventor Gabriel Danziger in May 1998 in a controlled environment in Mishmar Hashiva, Israel.

The first act of asexual reproduction of 'Dancasoft', was accomplished when vegetative cuttings were taken from the initial selection in June 1995 in a controlled environment in Mishmar Hashiva, Israel by a technician working under formulations established and supervised by the inventor. Horticultural examination of selected units initiated in September 1998 has demonstrated that the combination of characteristics of 'Dancasoft', as herein disclosed, are firmly fixed and are retained through successive generations of asexual reproduction.

'Dancasoft' has not been observed under all possible environmental conditions. The phenotype may vary somewhat with variations in environment such as temperature, light intensity and day length, however, without any variations in genotype. The following observations, measurements and comparisons describe the plants grown in Mishmar Hashiva, Israel under greenhouse conditions which approximate those generally used in commercial practice.

BRIEF DESCRIPTION OF THE INVENTION

The following traits have been repeatedly observed and are determined to be basic characteristics of 'Dancasoft' which in combination distinguish this petunia as a new and distinct cultivar:

1. Pastel pink flower color;
2. Single flower type;
3. Medium flower size;
4. Early, year round flowering time;
5. Spreading, well branched, vigorous growth habit;
6. Good weather tolerance; and
7. Suitable for hanging baskets and bedding.

Of the many commercial cultivars known to the present Inventor, the most similar in comparison to 'Dancasoft' is Chipper® by Daniziger "Dan" Flower Farm.

In comparisons to Chipper®, 'DANCASOFT' has brighter flower color, more upright growth habit, earlier flowering time, more flowers, and a longer flowering season.

BRIEF DESCRIPTION OF THE DRAWING

The accompanying photograhic drawings show typical flower and foliage characteristics of 'Dancasoft' with the color being as true as possible with illustrations of this type.

DETAILED BOTANICAL DESCRIPTION

In the following description color references are made to The Royal Horticultural Society Color Chart. The color values were determined between 10:00 a.m.–12:00 p.m. in October 2000 under full sunlight at Mishmar Hashiva, Israel.

Plant:

*Age.*—3 months.
*Growth habit.*—Trailing vigorously.
*Plant height.*—6–8 inch.
*Spreading area.*—30 inch.
*Blooming period.*—All year round in moderate climate.

Stem:
*Thickness.*—2 mm.
*Color.*—Yellow-Green 145A.
*Pubescence.*—Yes.
*Branching.*—Freely.
*Length of internode.*—20 mm.

Leaf:
*Arrangement on stem.*—Alternate.
*Shape.*—Elliptic.
*Apex.*—Acuminate.
*Base.*—Rounded.
*Margin.*—Entire.
*Venation.*—None.
*Size.*—Length 50 mm.
*Thickness.*—0.2 mm.
*Color.*—Green 137 B both surfaces.
*Markings.*—None.
*Pubescence.*—Yes.

Flower:
*Flower longevity.*—5–7 days.
*Fragrance.*—None.
*Orientation at opening.*—Upright.
*Type.*—Single.
*Shape.*—Regular, rounded, corolla tube.
*Diameter.*—45 mm.
*Petals.*—Number: 5 lobes united. Shape: Salver form. Size: 5.5 cm in length, 5.5 cm in width. Apex: Truncate. Margin: Entire. Texture: Smooth. Color: Red-purple, RHS 64 A (upper surface), RHS 65 D (lower surface).
*Sepals.*—Number: 5. Shape: Oblong. Size: 15 mm in length, 2 mm in width. Apex: Acuminate. Margin: Entire. Texture: Pubescent. Color: Green, RHS 144 A both surfaces.
*Bud.*—Shape: Oblong. Length: 4 cm. Diameter 6 mm. Color: Yellow-green, RHS 145 B.
*Peduncle length.*—15 mm.
*Peduncle color.*—Yellow-Green. 144 B.

Reproductive organs:
*Pistil.*—1, color yellow, 20 mm in length.
*Stigma.*—2 lobed, green RHS 143 B.
*Style.*—18 mm in length.
*Ovary.*—Yellow green RHS 144 B.
*Stamen.*—5.
*Anther.*—Yellow-orange RHS 19 B.
*Filament.*—Yellow-green RHS 145 B.
*Pollen.*—RHS 13 D, amount unquantifiable.
*Fruit.*—Number: Ten. Shape: Ovate. Size: 9 mm in length, 4 mm in diameter. Color: Greyed-orange, RHS 166 B.
*Seed.*—Number: 50–70. Shape: Rounded. Size: 1 mm in length, 1 mm in diameter. Color: Greyed-orange, RHS 165 A.

Pest/disease resistance: No observations made.

I claim:

1. A new and distinct cultivar of Petunia named 'Dancasoft', as described and illustrated.

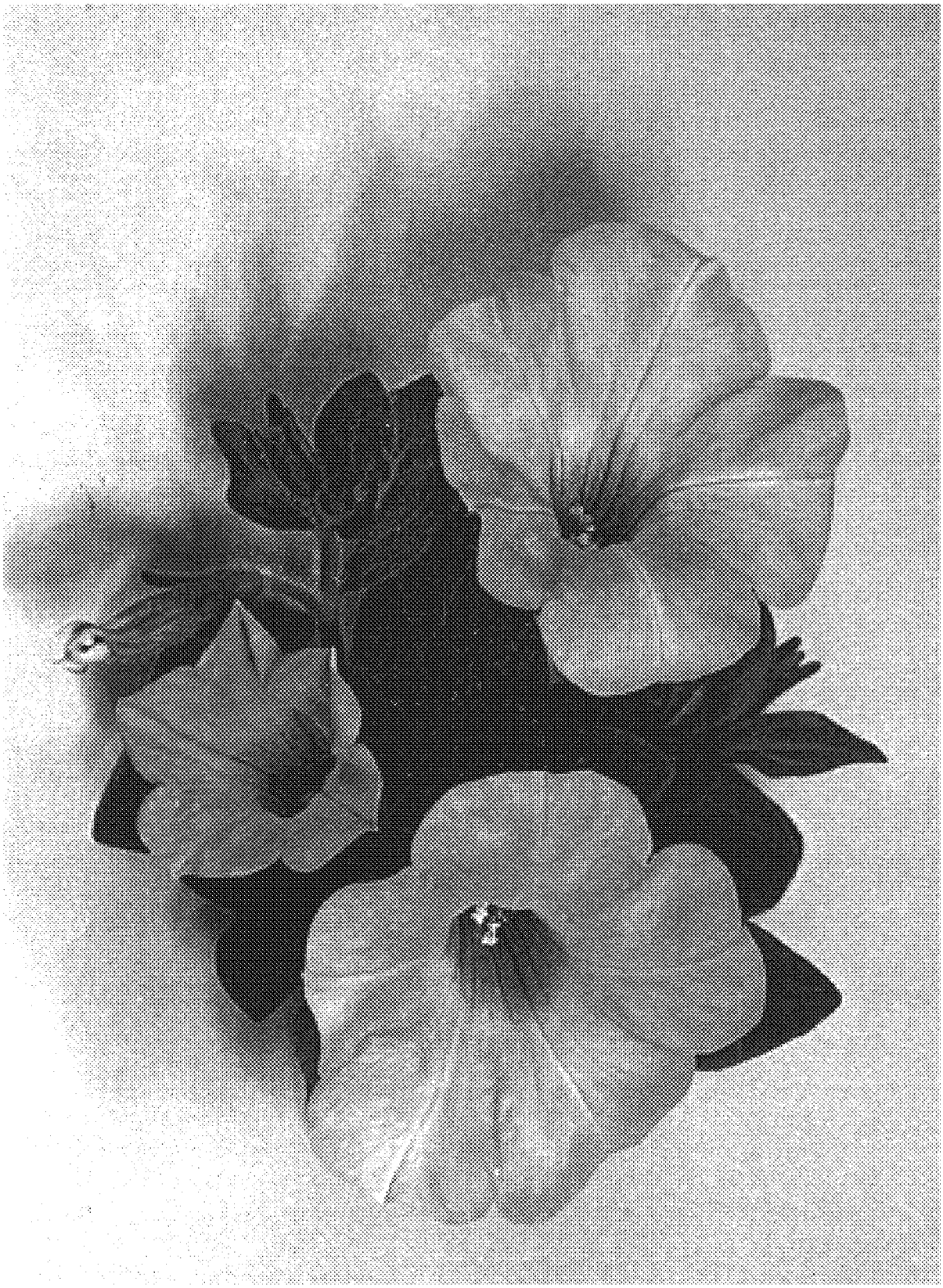

* * * * *